United States Patent [19]
Dalboege et al.

[11] Patent Number: 6,159,718
[45] Date of Patent: Dec. 12, 2000

[54] ENZYME WITH POLYGALACTURONASE ACTIVITY

[75] Inventors: Henrik Dalboege, Virum; Lene Nonboe Andersen, Birkeroed; Lene Venke Kofoed, Ugerloese; Markus Sakari Kauppinen, Copenhagen; Stephan Christgau, Vedbaek; Hans Peter Heldt-Hansen, Virum; Torben Halkier, Frederiksberg, all of Denmark

[73] Assignee: Novo Nordisk A/S, Bagsvaerd, Denmark

[21] Appl. No.: 09/087,194

[22] Filed: May 29, 1998

Related U.S. Application Data

[62] Division of application No. 08/448,624, filed as application No. PCT/DK93/00445, Dec. 23, 1993, abandoned.

[30] Foreign Application Priority Data

Dec. 23, 1992 [DK] Denmark ................................. 1545/92
Mar. 10, 1993 [DK] Denmark ................................. 0269/93
Oct. 28, 1993 [DK] Denmark ................................. 1215/93

[51] Int. Cl.$^7$ ............................. C07H 21/04; C12N 9/24; C12N 15/00; C12N 1/14; C12Q 1/68
[52] U.S. Cl. ........................ 435/200; 435/6; 435/252.3; 435/254.11; 435/320.1; 435/325; 536/23.2; 536/24.3
[58] Field of Search ............................. 435/6, 200, 252.3, 435/254.11, 320.1, 325; 536/23.2, 24.3

[56] References Cited

PUBLICATIONS

Plastow et al., Symbiosis, vol. 2, pp. 115–122 (1986).
Behere et al., Enzyme Microb. Technol., vol. 15, pp. 158–161 (1993).
Kester et al., Biotechnology and Applied Biochemistry, vol. 12, pp. 150–160 (1990).
Keon et al., Appl. Environ. Microbiol., vol. 56, No. 8, pp. 2522–2528 (1990).
Polizeli et al., Jour. Gen. Microbiol., vol. 137, pp. 1815–1823 (1991).
Siéssere et al., Jour. Gen. Microbiol., vol. 138, pp. 1801–1805 (1992).
Bussink et al., FEBS 08996, vol. 273, No. 1,2, pp. 127–130 (1990).
Bussink et al., Eur. J. Biochem., vol. 208, pp. 83–90 (1992).
Bussink et al., Curr Genet, vol. 19., pp. 467–474, (1991).
M.S. Foda, et al., Mikrobiol., 139, p. 463–469 (1984).
Pasculli et al., Lebensm–Wiss. u–Technol., vol. 24, p. 63–70 (1991).

*Primary Examiner*—Lisa Jo Hobbs
*Attorney, Agent, or Firm*—Steve T. Zelson; Carol E. Rozek; Cheryl E. Agreo

[57] ABSTRACT

An enzyme exhibiting polygalacturonase activity, which enzyme is immunologically reactive with an antibody raised against a purified polygalacturonase derived from *Aspergillus aculeatus*, CBS 101.43. The enzyme may be produced by recombinant DNA techniques and may be used for degradation of plant cell walls, for instance in the wine and juice production.

24 Claims, 9 Drawing Sheets

1 2 3 4 5

ENZYME WITH POLYGALACTURONASE ACTIVITY

CROSS-REFERENCE TO RELATED APPLICATIONS

This application is a division of application Ser. No. 08/448,624 filed on Jun. 6, 1995, now abandoned, which is the National Stage application of PCT/DK93/00445, filed Dec. 23, 1993, and claims priority under 35 U.S.C. 119 of Danish application Ser. Nos. 1545/92 filed on Dec. 23, 1992, 0269/93 filed on Mar. 10, 1993, and 1215/93 filed on Oct. 28, 1993, the contents of which are fully incorporated herein by reference.

FIELD OF INVENTION

The present invention relates to an enzyme with polygalacturonase activity, a method of producing the enzyme, and an enzyme preparation containing the enzyme.

BACKGROUND OF THE INVENTION

Pectin polymers are important constituents of plant primary cell walls. They are mainly composed of chains of 1,4-linked α-D-galacturonic acid and methoxylated derivatives thereof. The use of pectin-degrading enzymes is important for the food industry, primarily in fruit and vegetable processing such as fruit juice production or wine making, where their ability to catalyse the degradation of the backbone of the pectin polymer is utilised.

Multiple pectin degrading enzymes is known to be present in various microorganisms such as *Aspergillus niger*. Of these, pectin methylesterase catalyses the removal of methanol from pectin, resulting in the formation of pectic acid (polygalacturonic acid). Pectate lyase cleave galacturonosyl bonds in polygalacturonic acid by β-elimination, pectin lyase cleave the galacturonosyl bonds of highly methylated pectins by β-elimination, and polygalacturonase hydrolyses the glycosidic linkages in the polygalacturonic acid chain.

For many purposes, it would be desirable to provide each of the pectin degrading enzymes present in, for instance, commercial preparations containing a number of different pectin degrading enzymes (an example of such a preparation is Pectinex Ultra SP®, prepared from *Aspergillus aculeatus*, available from Novo Nordisk A/S) in a form free from other components. In this way, it would be possible to produce enzyme preparations adapted to specific purposes, such preparations either containing a single pectin degrading enzyme or arbitrary combinations thereof. To serve this end, it is convenient to provide single-component pectin degrading enzymes by recombinant DNA techniques.

Plastow et al. (1986) describe the cloning of four pectate lyase genes and one polygalacturonase gene from Erwinia in *E. coli*. A cloned polygalacturonase from *Erwinia carotovora* is described in WO 91/043 ino. U.S. Pat. No. 4,801,540 (Calgene) describes a DNA sequence encoding a tomato polygalacturonase and its expression in plants.

Behere et al. (1993), Kester and Visser (1990), Keon and Waksman (1990), Lourdes et al. (1991), and Siéssere et al. (1992) disclose the characterization of polygalacturonases isolated from various fungal species including *A. niger*. Cloning, expression and further characterization of polygalacturonases from *A. niger* are described in EP 421 919 (Ciba-Geigy) and by Bussink et al. (1990), Bussink et al. (1991) and Bussink et al. (1992).

SUMMARY OF THE INVENTION

It is an object of the present invention to prepare single-component polygalacturonases.

Accordingly, the present invention relates to an enzyme exhibiting polygalacturonase activity, which enzyme is immunologically reactive with an antibody raised against a purified polygalacturonase derived from *Aspergillus aculeatus*, CBS 101.43.

In the present context, the term "derived from" is intended not only to indicate a polygalacturonase produced by strain CBS 101.43, but also a polygalacturonase encoded by a DNA sequence isolated from strain CBS 101.43 and produced in a host organism transformed with said DNA sequence.

In another aspect, the invention relates to an enzyme exhibiting polygalacturonase activity, which enzyme is encoded by a DNA sequence comprising at least one of the following partial sequences

| | | |
|---|---|---|
| (a) | CCAACAATGC ACCTTAACAC | (SEQ ID NO: 1) |
| (b) | CACCCTACTC GTCTCGCTCG | (SEQ ID NO: 2) |
| (c) | CCCTCGGGCG CGCGAGCGTC | (SEQ ID NO: 3) |
| (d) | CTCGCCAGCC CAGCCCCACC | (SEQ ID NO: 4) |
| (e) | AGCAATCACG GCCCCGCCCA | (SEQ ID NO: 5) |
| (f) | CGGCCGAGGA GATCGCGAAG | (SEQ ID NO: 6) |
| (g) | GCGACGACCT GCACGTTCTC | (SEQ ID NO: 7) |
| (h) | CGGATCGAAC GGCGCCTCGT | (SEQ ID NO: 8) |
| (i) | CGGCCAGCAA GTCAAGACCT | (SEQ ID NO: 9) |
| (j) | GTGCTCGACC ATGTGTTGTG | (SEQ ID NO: 10) |
| (k) | AATGTGCCGT TCCGTGCG | (SEQ ID NO: 11) |
| (l) | GTTCTCTCTT TCGATTCTGT | (SEQ ID NO: 12) |
| (m) | TGATCAGACA CTCATTCCTT | (SEQ ID NO: 13) |
| (n) | CCTTTATTCA CTCTTTATCA | (SEQ ID NO: 14) |
| (o) | CGATTCTGTT TGACCAGAAT | (SEQ ID NO: 15) |
| (p) | CCATCATGCA CTCCTTCCAG | (SEQ ID NO: 16) |
| (q) | CTTCTCGGCC TGGCGCCTGT | (SEQ ID NO: 17) |
| (r) | CGGCTCCGTC GTCTCGGCCG | (SEQ ID NO: 18) |
| (s) | CTCCTACTGC GTCTCGTGTC | (SEQ ID NO: 19) |
| (t) | TCCGACCTTG TGAAGAATCC | (SEQ ID NO: 20) |
| (u) | TCTTCTACCT GCACTTTCAC | (SEQ ID NO: 21) |
| (v) | CTCTGCCAGC GAGGCTAGCG | (SEQ ID NO: 22) |
| (w) | AAACGTCTTC TTCGTGCTCC AACGTC | (SEQ ID NO: 23) |
| (x) | ACATTCACAC TCCCTCATAA | (SEQ ID NO: 24) |
| (y) | AATCTCTTTA CACCTGCTCA | (SEQ ID NO: 25) |
| (z) | CCCTCTGTCA TTCTTTATTC | (SEQ ID NO: 26) |
| (aa) | TTTCCTACCA ACAAAAATGG | (SEQ ID NO: 27) |
| (bb) | TTCGTCAGCT TGCATTGGCC | (SEQ ID NO: 28) |
| (cc) | TGCGGACTGC TGGCAGCAGT | (SEQ ID NO: 29) |
| (dd) | GGCCGTCCAG GCAGCCCCCG | (SEQ ID NO: 30) |

-continued (ee) CGGAACCGGC TGATCCGAAG        (SEQ ID NO: 31)

(ff) GGTGACTGAA TCGCCG            (SEQ ID NO: 32)

In a further aspect, the invention relates to an enzyme exhibiting polygalacturonase activity, which enzyme is encoded by a DNA sequence comprising or included in at least one of the following partial sequences

```
ACCAAGACAACCCGAAGCTTGAACCCTCTTGGCCCAAATCCAACAATGCACCTTAACACCA    (SEQ ID NO: 33)

CCCTACTCGTCTCGCTCGCCCTCGGGCGCGCGAGCGTCCTCGCCAGCCCAGCCCCACCAGC

AATCACGGCCCCGCCCACGGCCGAGGAGATCGCGAAGGCGACGACCTGCACGTTCTCCGGA

TCGAACGGCGCCTCGTCGGCCAGCAAGTCAAGACCTGTGCTCGACCATGTGTTGTGAATGT

GCCGTTCCGTGCG or

AAGTCTCGCGCGCACAGCCTGACCAACTCGGTGATTCAGCGGCTGAAGATCGTCAACTCGC    (SEQ ID NO: 34)

CGGTGCAGGTTTTCACGTTGCGGGGTCGGATTATCTGACCCTCAAGGATATCACGATCGAC

AACTCGGACGGCGACGACAATGGCGGGCATAATACCGATGCGTTTGATATCGGCACGAGCA

CGTATGTCACGATCTCGGGCGCCACGGTGTATAATCAGGATGATTTGCGTGGGCTGTGTAA

TTCGGGGGGAATATCTACTTCTCGGGCGGCCTACTGCTCCGGTGGACACGGCTTGTCCATT

GGTTCGGTGGGCGGACGCAGTGATAATACGGTTAAGAACGTGACGTTTGTGGATTCGACGA

TCATTAACTCAGATAATCGGTCCGCAATCAAAACCAACATCGACACCACCGGCTCCGTGTC

CGACGTCACCTACAAGGACATCACGCTCACCTCCATCGCCAAGTACGGGATCGTGGTGCAG

CAGAACTACGGCGACACGTCATCGACGCCCACGACGGGGGTGCCGATCACGGACTTTGTGC

TGGACAACGTGCACGGCTCGGTGGTCAGCTCGGGGACCAACATCCTCATCTCGTGCGGGGT

CGGGCAGTTGTTCGGATTGGAGTGGACGGATGTGAGTGTCAGTGGGGGGAAGACGAGTTCC

AAGTGTACGAATGTGCCGAGTGGGGCTAGTTGTTGATTCTCTGGTTGTTTGTGGTTGAGAG

GGGGAGGGGGGTGATTTCTCAAGCTGGAAGGGGTTCTTCGAGCTTAGGAGGTCTCAGGCT

TAGTTTGGAGAGCGGAACGGGTCTCTTGACTACTTAGGTTGCTCTTGTTTGAATGGGAAAA

AAAAAAAAA
``` or a sequence homologous thereto encoding a polypeptide with polygalacturonase activity. This enzyme termed is polygalacturonase I (or PG I) in the following disclosure.

In a still further aspect, the invention relates to an enzyme exhibiting polygalacturonase activity, which enzyme is encoded by a DNA sequence comprising or included in the following partial sequence or a sequence homologous thereto encoding a polypeptide with polygalacturonase activity. This enzyme is termed polygalacturonase II (or PG II) in the following disclosure.

In a still further aspect, the invention relates to an enzyme exhibiting polygalacturonase activity, which enzyme is encoded by a DNA sequence comprising or included in at least one of the following partial sequences

```
GTTCTCTCTTTCGATTCTGTTGATCAGACACTCATTCCTTCCTTTATTCACTCTTTATCAC    (SEQ ID NO: 35)

GATTCTGTTTGACCAGAATCCATCATGCACTCCTTCCAGCTTCTCGGCCTGGCGCCTGTCG

GCTCCGTCGTCTCGGCCGCTCCTACTGCGTCTCGTGTCTCCGACCTTGTGAAGAATCCTCT

TCTACCTGCACTTTCACCTCTGCCAGCGAGGCTAGCGAAACGTCTTCTTCGTGCTCCAACG

TGGTCCTCAGCAACATGAGGTGCCCGCCGGAGAGACACTTGACCTGTCGACAGCGCTGACG

GGTGCCACCATCACTTTTGAGGGTACCACCAGCTTCGGCTACGAGGAATGGGATGGTCTCT

TATCCGTTTCGGCGGAACGAGCATCACCATCACCCAGTCTGACGGTGCTGTCATTGACGG
```

```
AAAGACATTCACACTCCCTCATAAAATCTCTTTACACCTGCTCACCCTCTGTCATTCTTTA    (SEQ ID NO: 36)

TTCTTTCCTACCAACAAAAATGGTTCGTCAGCTTGCATTGGCCTGCGGACTGCTGGCAGC

AGTGGCCGTCCAGGCAGCCCCCGCGGAACCGGCTGATCCGAAGGGTGACTGAAGCGCCGGA

CGCCAGCCTCCTCCACAAGCGAGCCACCACTTGCACCTTCTAGGCTCTGAGGGAGCTTCAA or

CCATATCACTGGCGTTCCCATCACGGATTTCACCCTCGAGAACGTGATTGGTACTTGTGCG    (SEQ ID NO: 37)

GACGACGACTGCACCGAGGTTTACATTGCGTGTGGTAGTGGCGCCTGCTCGAACTGGAGCT

GGTCCAGCAGTGAAGTGTCACGGGCGGCAAGGTCGAGCTCCAAGTGCCTGAATGTCTTCCG

GATAAGCTGCGACTTGTAGGGGACTTTGCCGCTGGAGTCGGCTGGACTTCCCAGGGAACTG

TTCTATCTCGCTATGGCTGTGGACGTACCAGGACATGCCACCAAGCGCCTAGTCAACATAT

CTATCTTCTGCCAAATGAATACTAATTTCCAAAAAAAAAAAAAA
``` or a sequence homologous thereto encoding a polypeptide with polygalacturonase activity. This enzyme is termed polygalacturonase III (or PG III) in the following disclosure.

In the present context, the term "homologue" is intended to indicate a polypeptide encoded by DNA which hybridizes to the same probe as the DNA coding for the polygalacturonase enzyme under certain specified conditions (such as presoaking in 5×SSC and prehybridizing for 1 h at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at ~40° C. followed by washing three times in 2×SSC, 0.2% SDS at 40° C. for 30 minutes). More specifically, the term is intended to refer to a DNA sequence which is at least 70% homologous to the sequence shown above encoding the polygalacturonase of the invention, such as at least 75%, at least 80%, at least 85% at least 90% or even at least 95% homologous to any of the sequences shown above. The term is intended to include modifications of the DNA sequence shown above, such as nucleotide substitutions which do not give rise to another amino acid sequence of the polygalacturonase, but which correspond to the codon usage of the host organism into which the DNA construct is introduced or nucleotide substitutions which do give rise to a different amino acid sequence and therefore, possibly, a different protein structure which might give rise to a polygalacturonase mutant with different properties than the native enzyme. Other examples of possible modifications are insertion of one or more nucleotides into the sequence, addition of one or more nucleotides at either end of the sequence, or deletion of one or more nucleotides at either end or within the sequence.

In still further aspects, the present invention relates to an enzyme preparation useful for the degradation of plant cell wall components, said preparation being enriched in an enzyme exhibiting polygalacturonase activity as described above, and to various uses of said enzyme preparation.

DETAILED DESCRIPTION OF THE INVENTION

Figure 1:
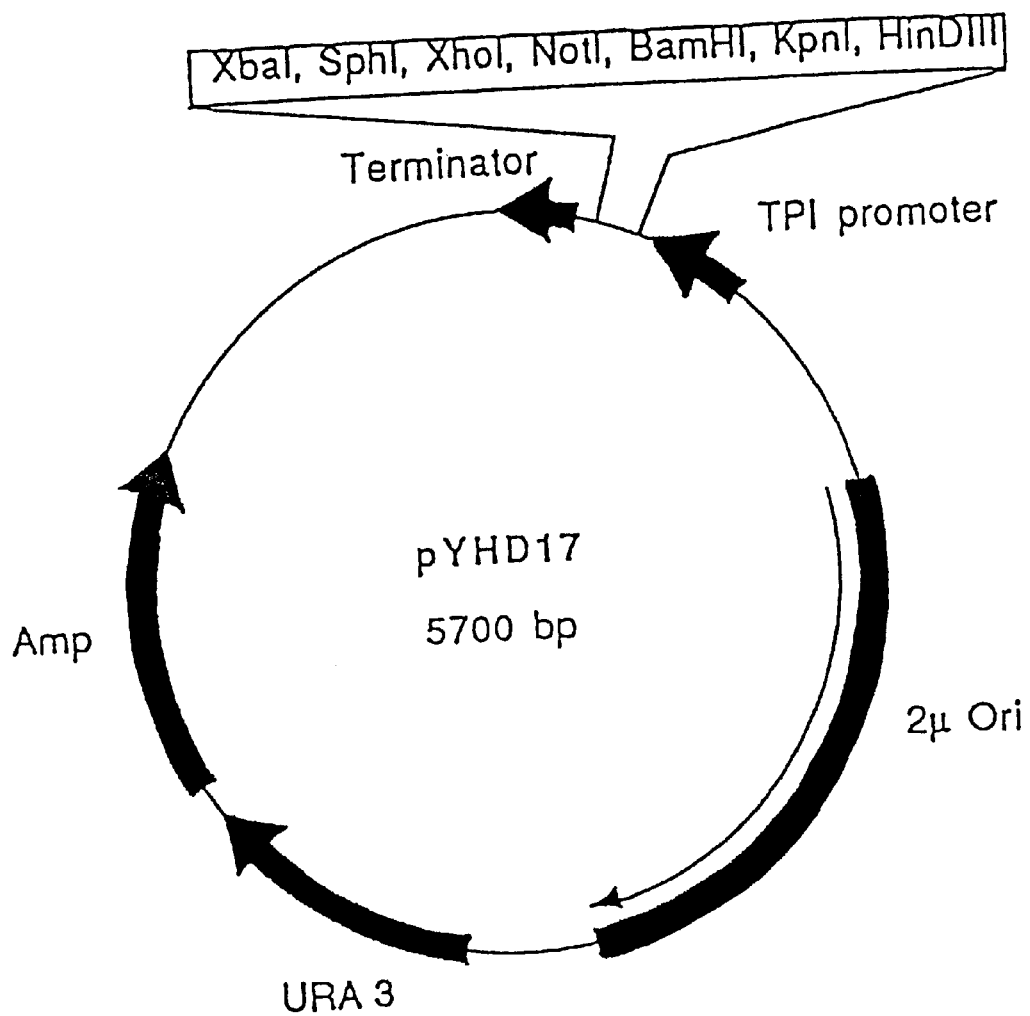

It has surprisingly been found that the partial sequence shown above encoding Polygalacturonase I of the present invention displays only limited homology with any previously characterized polygalacturonase be it of plant or microbial origin. Furthermore, as far as the present inventors are aware PG I is the first known microbial polygalacturonase which has a broad pH activity profile (PG I exhibits a considerable (more than 90%) activity in the pH range of 4.5–6.5), and which has a Ph optimum above 5.5. In contrast, the polygalacturonases from A. niger has been shown to have a Ph optimum of between 4–5 (cf. Keon and Waksman 1990). This makes the PG I of the invention particularly suitable for enzymatic treatments to be performed at pH above 4.5 such as the manufacture of carrot or potato purees as well as the treatment of soy beans or beets for feed. Furthermore, PG I is particularly well suited for applications, in which the pH changes during the operation due to its extraordinary broad pH optimum.

It is contemplated that polygalacturonases having a similar pH activity profile to that of PG I may be encoded by a DNA sequence which a) hybridizes to the same oligonucleotide probe as the DNA sequence encoding PG I of the present invention and/or is immunologically reactive with an antibody raised against the purified PG I of the invention.

Furthermore, as regards PG II of the present invention, said enzyme has surprisingly been found to exhibit a higher specific activity than that described for any other microbial, in particular A. niger polygalacturonase. Thus, the specific activity of the PG II of the invention has been found to be in the range of 1500–1695 µmol/min/mg (determined by the method described in Example 3 herein). As far as the present inventors are aware PG II of the present invention is the first polygalacturonase which has been found to have a specific activity which is higher than 800 µmol/min/mg (as determined by the method disclosed herein), in particular higher than 1000 µmol/min/mg such as higher than 1500 µmol/min/mg, e.g. a specific activity in the range of 1000–2000 µmol/min/mg, such as 1500–2000 µmol/min/mg.

The enzyme of the invention may be isolated by a general method involving cloning, in suitable vectors, a DNA library from Aspergillus aculeatus, transforming suitable yeast host cells with said vectors, culturing the host cells under suitable conditions to express any enzyme of interest encoded by a clone in the DNA library, and screening for positive clones by determining any polygalacturonase activity of the enzyme produced by such clones.

A more detailed description of this screening method is given in Example 1 below.

The DNA sequence coding for the enzyme may for instance be isolated by screening a cDNA library of

*Aspergillus aculeatus*, e.g. strain CBS 101.43, publicly available from the Centraalbureau voor Schimmelcultures, Delft, NL, and selecting for clones expressing the appropriate enzyme activity (i.e. polygalacturonase activity as defined by the ability of the enzyme to hydrolyse glycosidic bonds in the galacturonic chains of pectin). The appropriate DNA sequence may then be isolated from the clone by standard procedures, e.g. as described in Example 1. It is expected that DNA encoding a homologous enzyme may be isolated by similarly screening a cDNA library of another microorganism, in particular a fungus, such as a strain of an Aspergillus sp., in particular a strain of *A. aculeatus* or *A. niger*, a strain of a Trichoderma sp., in particular a strain of *T. harzianum* or *T. reesie*, a strain of a Fusarium sp., in particular a strain of *F. oxysporum*, a strain of a Humicola sp., or a strain of Geotricum sp. Alternatively, the DNA coding for a polygalacturonase of the invention may, in accordance with well-known procedures, conveniently be isolated from DNA from any of the above mentioned organisms by use of synthetic oligonucleotide probes, prepared on the basis of a DNA sequence disclosed herein. For instance, a suitable oligonucleotide probe may be prepared on the basis of any of the partial nucleotide sequences (a)–(ff) listed above.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the polygalacturonase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the polygalacturonase, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y. 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed polygalacturonase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified polygalacturonase may be employed for immunization of animals for the production of antibodies. More specifically, antiserum against the polygalacturonase of the invention, e.g. PG I, PG II or PG III, may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27– ino). Purified immunoglobulins may be obtained from the antisera, for example by salt precipitation (($NH_4)_2SO_4$), followed by dialysis and ion exchange chromatography, e.g. on DEAE-Sephadex. Immunochemical characterization of proteins may be done either by Outcherlony double-diffusion analysis (O. Outcherlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

In a still further aspect, the present invention relates to an enzyme preparation useful for the degradation of plant cell wall components, said preparation being enriched in an enzyme exhibiting polygalagturonase activity as described above. The enzyme preparation is of particular use in the processing of fruits, vegetables and other plant materials.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex® or Pectinex Ultra SP® (Novo Nordisk A/S). In the present context, the term "enriched" is intended to indicate that the pectin-degrading activity of the enzyme preparation has been increased, e.g. with an enrichment factor of 1.1, conveniently due to addition of an enzyme of the invention prepared by the method described above.

Alternatively, the enzyme preparation enriched in an enzyme exhibiting polygalacturonase activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

When the enzyme of the invention is to be used in the processing of fruits, vegetables and other plant materials, it may advantageously be used together with other enzymes, especially other pectin degrading enzymes. Accordingly, the enzyme preparation of the invention may in addition to the polygalacturonase comprise a cellulase, a xylanase, a protease, a pectin degrading enzyme, such as a pectin methyl esterase, a pectin lyase, pectin acetyl esterase, a rhamnogalacturonase, a galactanase, an arabinanase and/or a rhamnogalacturonan acetyl esterase.

Examples are given below of preferred uses of an enzyme preparation of the invention comprising an enzyme exhibiting polygalacturonase activity, optionally in combination with one or more other enzymes. The dosage of the enzyme preparation of the invention and other conditions under which the preparation is used may be determined on the basis of methods known in the art.

The enzyme preparation may be used for the treatment of pectin containing plant material, e.g. obtained from soy beans, sugar beets, apples or pears, so as to reduce the viscosity and thus improve the processing or appearance of the plant material in question. The viscosity reduction may be obtained by treating the pectin-containing plant material with an enzyme preparation of the invention under suitable conditions for full or partial degradation of the pectin-containing material. For instance, the enzyme preparation may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

The enzyme preparation may be used in the production of citrus juice, e.g. for partial or complete degradation of the pulp present in the juice after pressing. For this purpose polygalacturonase may be used alone.

By use of an enzyme preparation of the invention it is possible to regulate the consistency and appearance of processed fruit or vegetables. Thus, the consistence and appearance have been shown to be a product of the actual combination of enzymes used for the processing, i.e. the nature of the enzymes (especially pectin degrading enzyme (s)) with which the polygalacturonase of the invention is combined.

Examples of products with specific properties which may be produced by use of an enzyme preparation of the invention include clear juice, e.g. from apples, pears or berries, cloud stable juice, e.g. from apples, pears, berries, citrus, or tomatoes, and purees, e.g. from carrots and tomatoes.

From the foregoing disclosure it will be apparent that the polygalacturonase of the invention may be produced as a single component essentially free from other enzyme activities such as pectin esterase and/or pectin lyase activity, normally found to be present in commercially available polygalacturonase containing pectinolytic preparations.

On this basis the use of the polygalacturonase of the invention is especially advantageous for purposes in which the action of such other enzyme activities are undesirable. Examples of such purposes include the production of cloud stable juices and the production of purees. In these productions, the presence of, e.g., pectin esterase normally found as a side-activity in conventional pectinolytic enzyme preparations results in a decreased stability of the cloud in cloud stable juice or causes syneresis in puree.

Furthermore, due to its substantial purity the polygalacturonase of the invention can be used to modify pectin in such a way that the parts of the pectin which contains several adjacent non-methoxylated galacturonic groups will be degraded. If pectin esterase or pectin lyase activities were present, e.g. as it is the case for the enzyme preparation described in WO 89/12648, a more extensive degradation of the pectin would be obtained with a resulting reduction in the viscosifying ability of the pectin. By use of the polygalacturonase of the invention calcium mediated gelformation during e.g. mixing procedures may be prevented and the viscosifying ability of highly esterified pectin may be reduced only slightly.

The polygalacturonase of the invention can alone or together with other enzymes be used to improve the digestibility of pectin containing animal feed, e.g. feed prepared from soya beans, sugar beets or rape seeds. For this purpose, an enzyme preparation of the invention is added to the feed.

The polygalacturonase can alone or together with other enzymes be used to produce monogalacturonic acid or galacturonic acid containing oligosaccharides from pectin-containing material such as sugar beet pulp in accordance with well-known methods. Monogalacturonic acid may be used for production of galacturonic acid or for production of fatty acid and fatty alcohol esters and/or ethers of galacturonic acid. Galacturonic containing oligosaccharides may be used as additives for human food or animal feed.

Furthermore, the polygalacturonase can as such or in combination with other enzymes be used for the removal of pectic substances from plant fibres, which removal is essential, e.g. in the production of textile fibres or other cellulosic materials. For this purpose plant fibre material is treated with a suitable amount of the polygalacturonase of the invention under suitable conditions for obtaining full or partial degradation of pectic substances associated with the plant fibre material.

The invention is further described in the accompanying drawing in which

Figure 2:
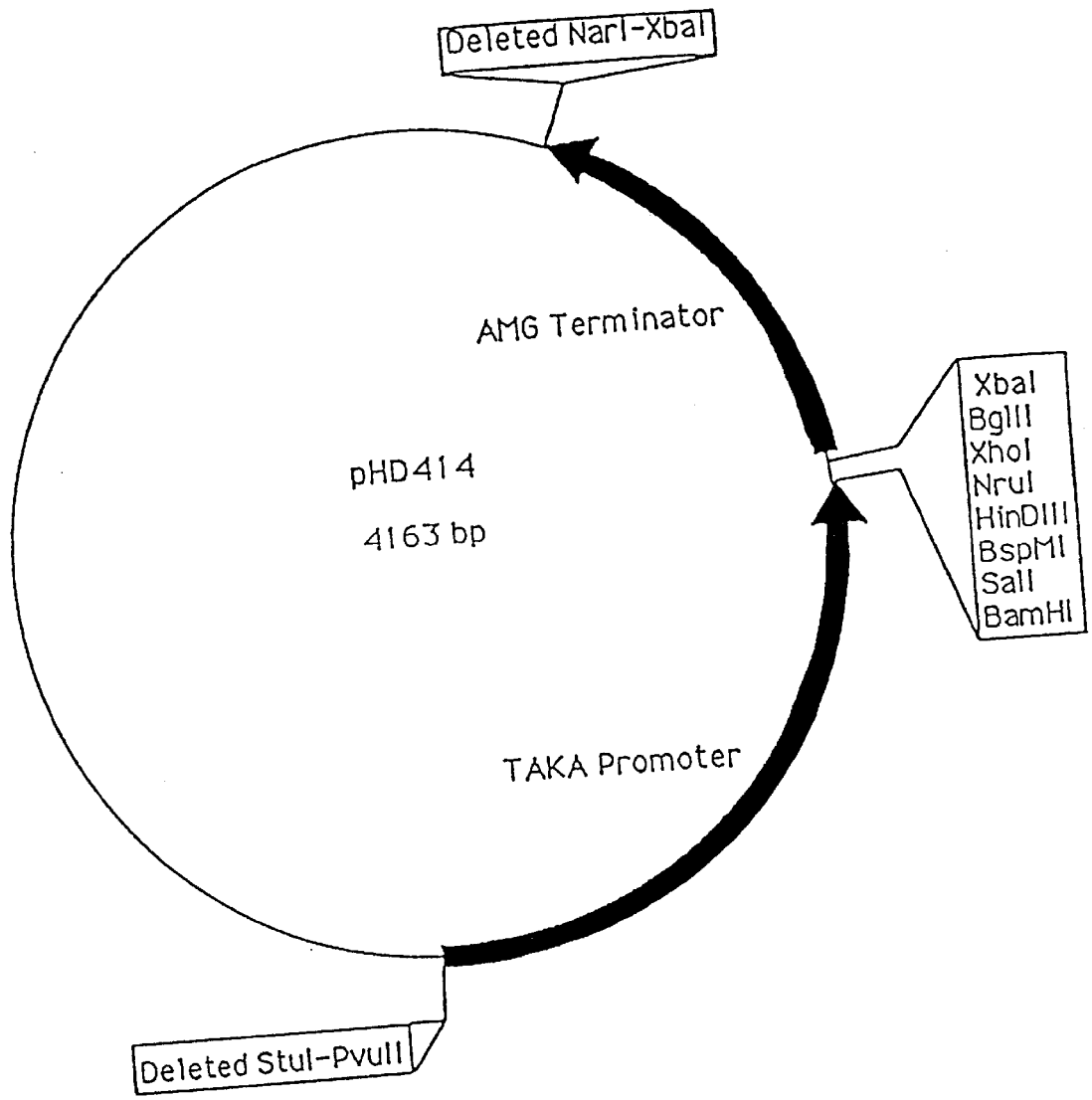
Figure 3A:
Figure 3B:
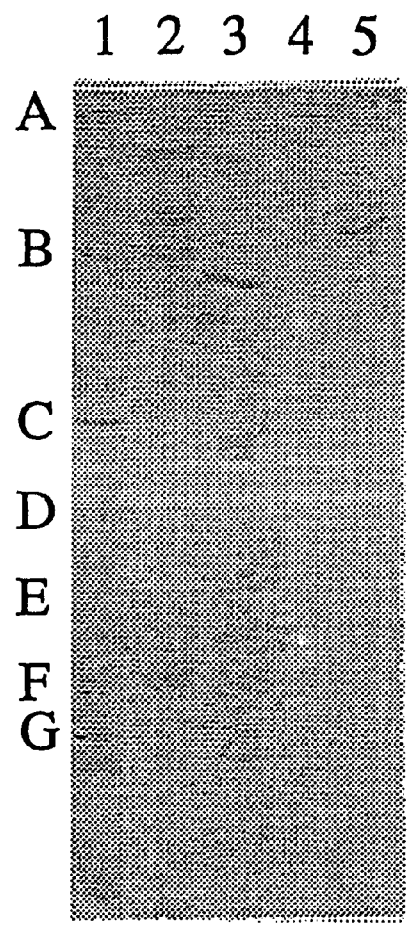
Figure 4:
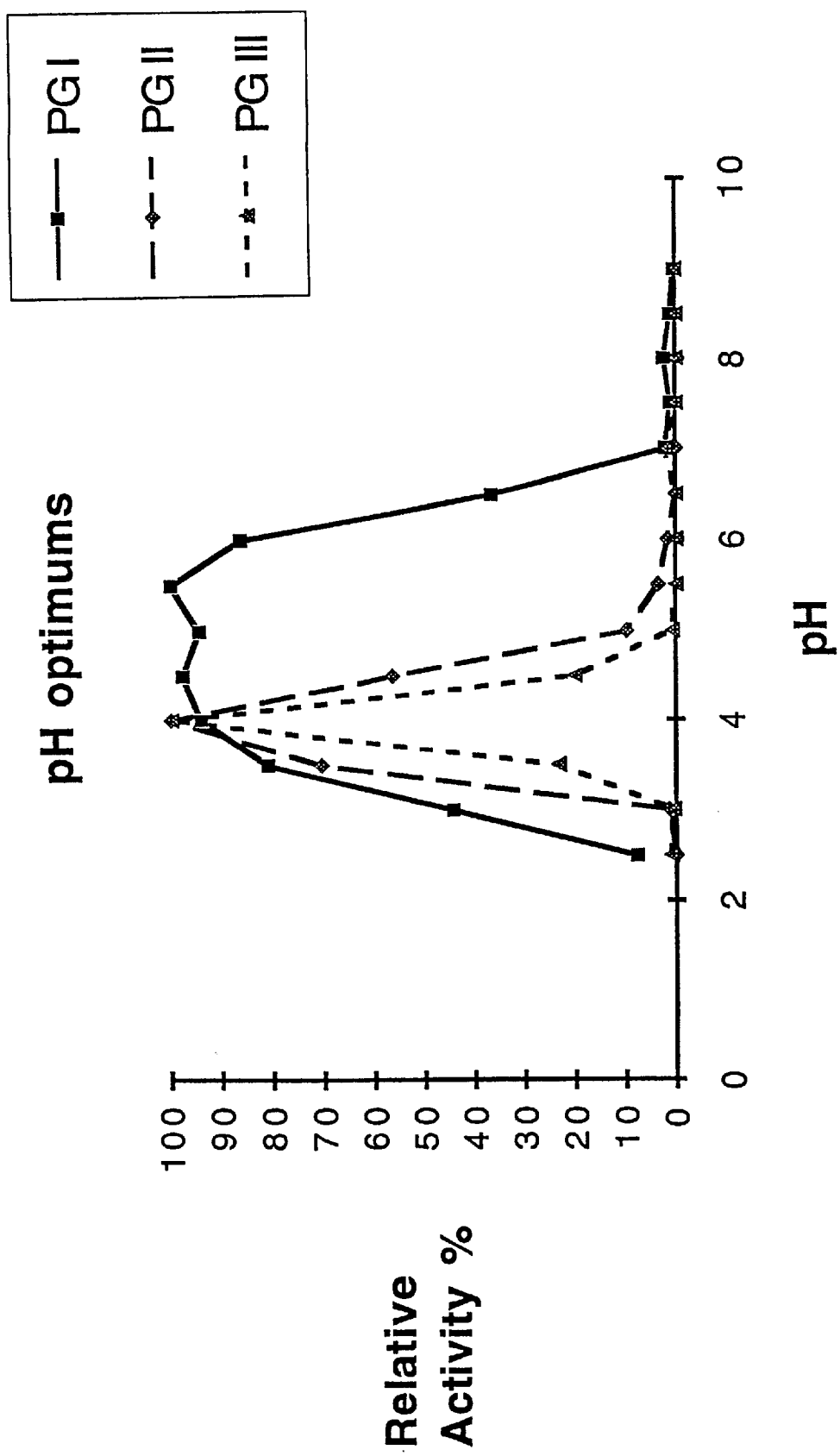
Figure 5:
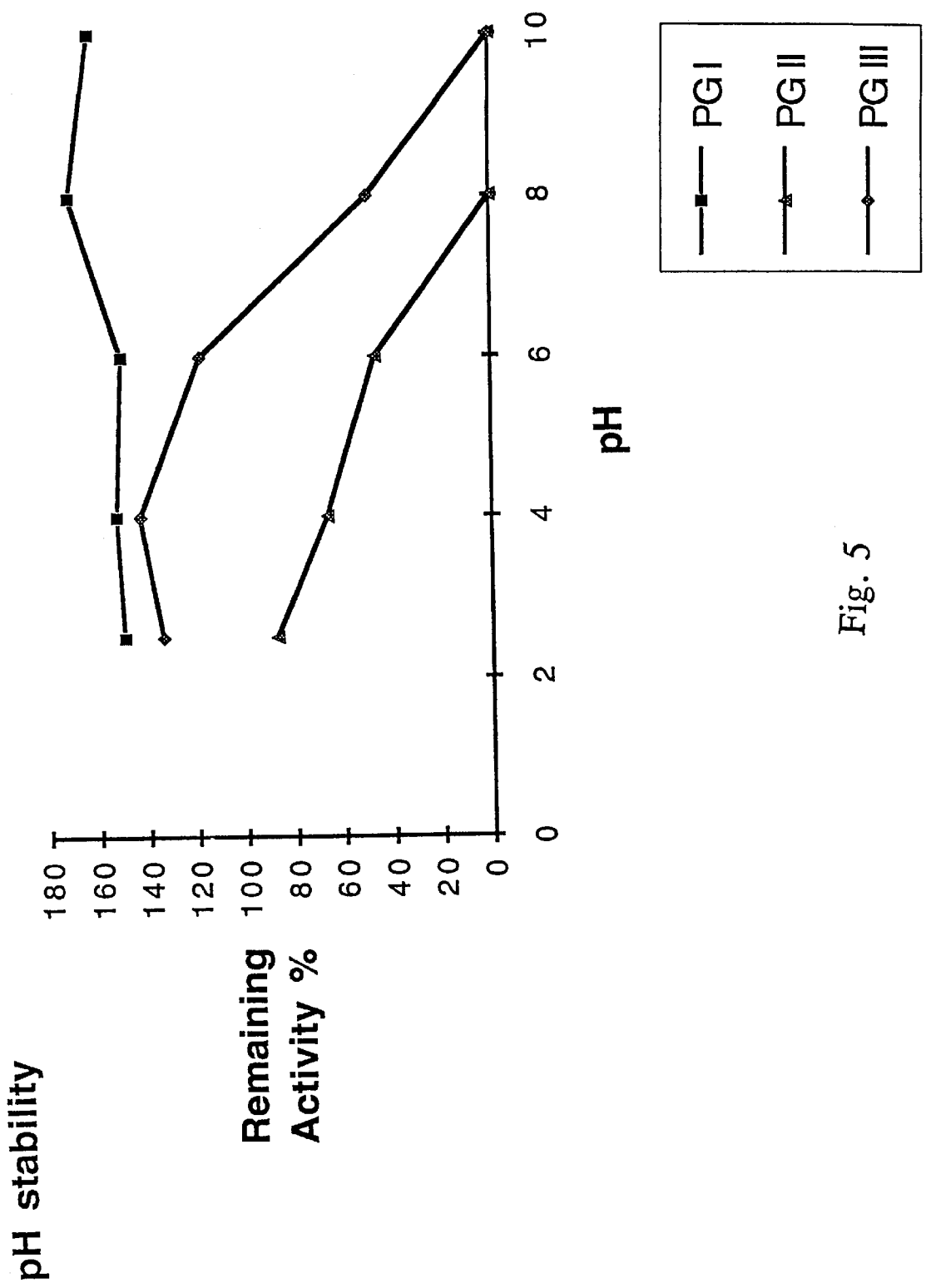
Figure 6:
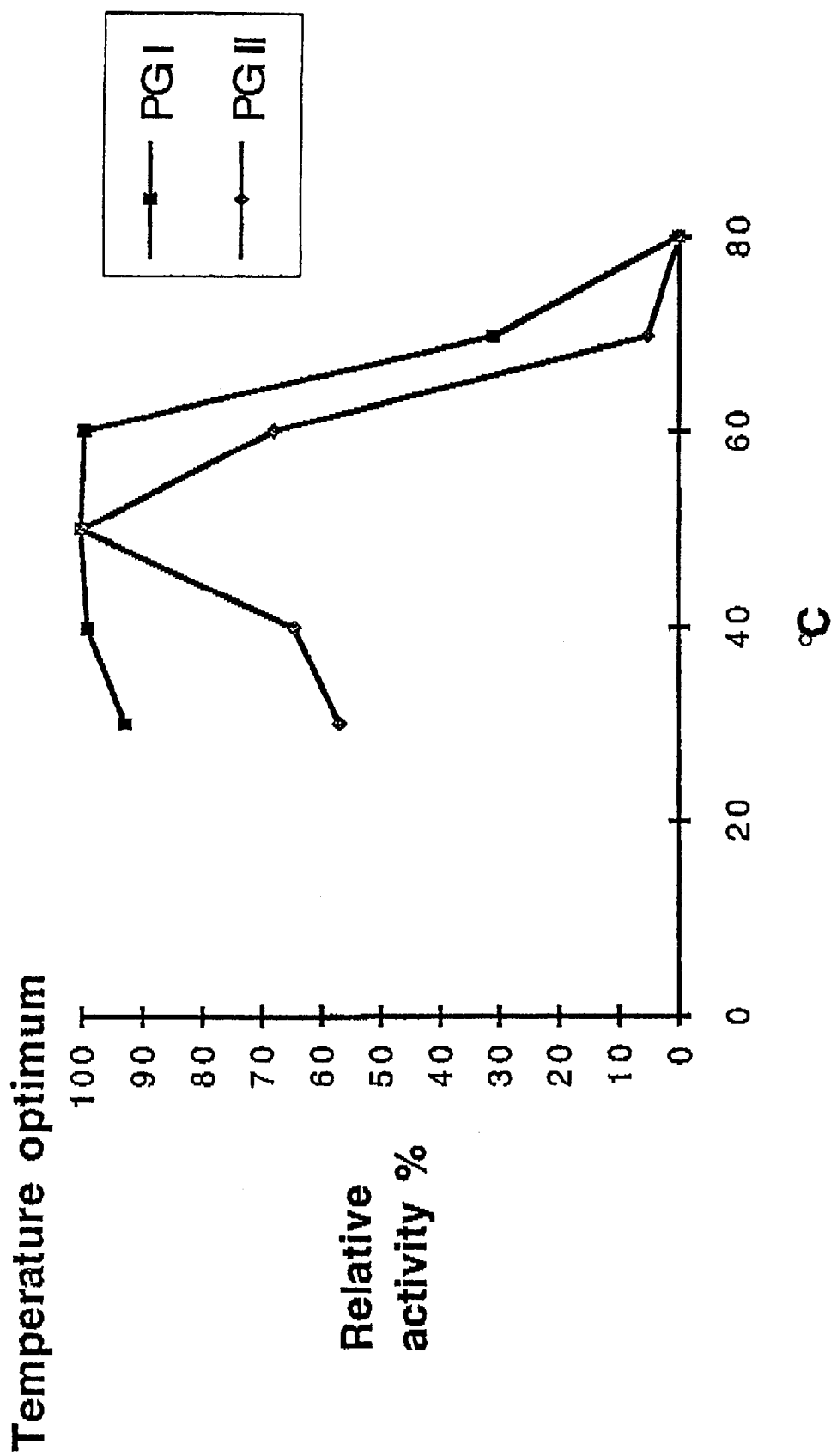
Figure 7:
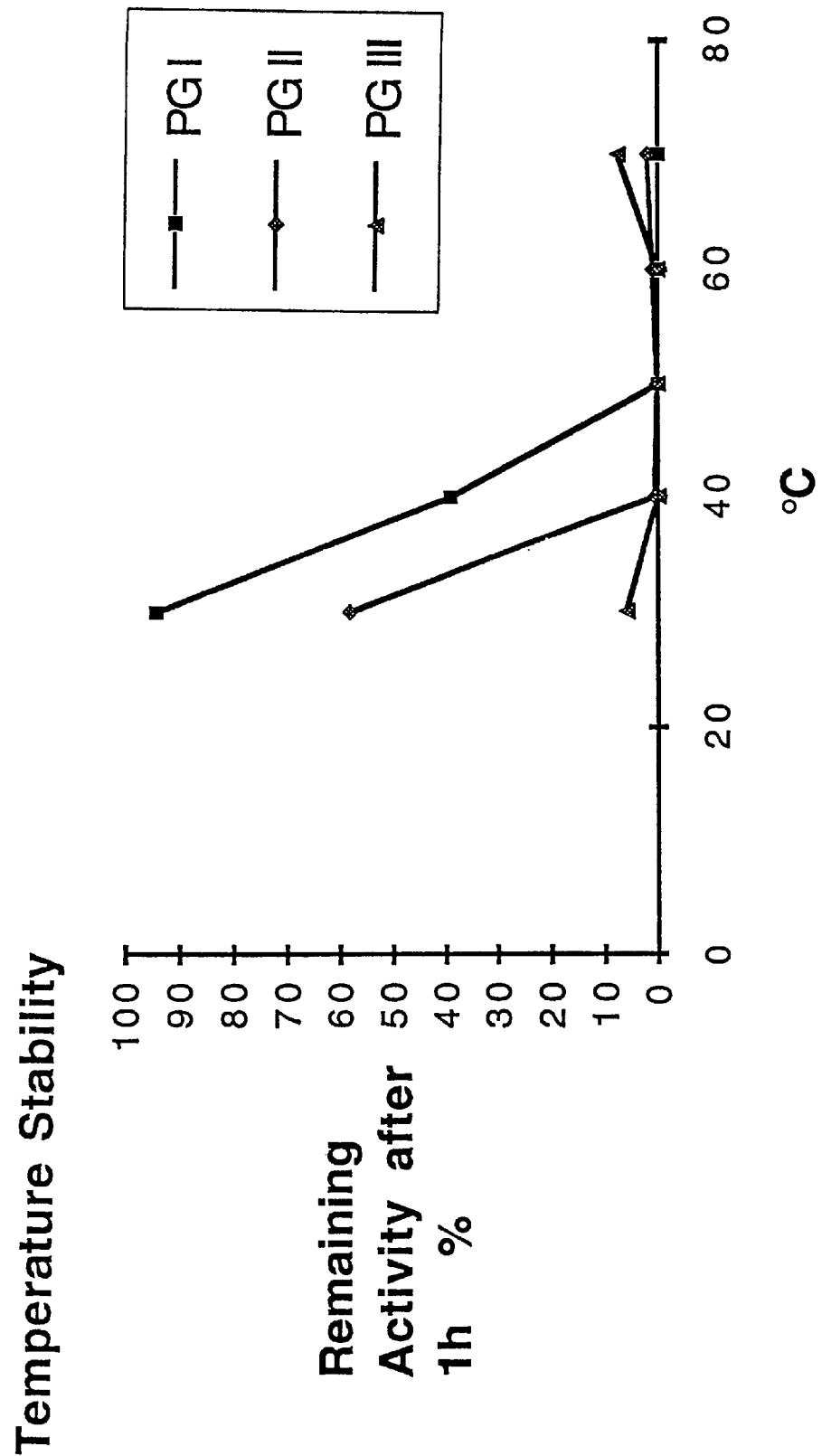
Figure 8:
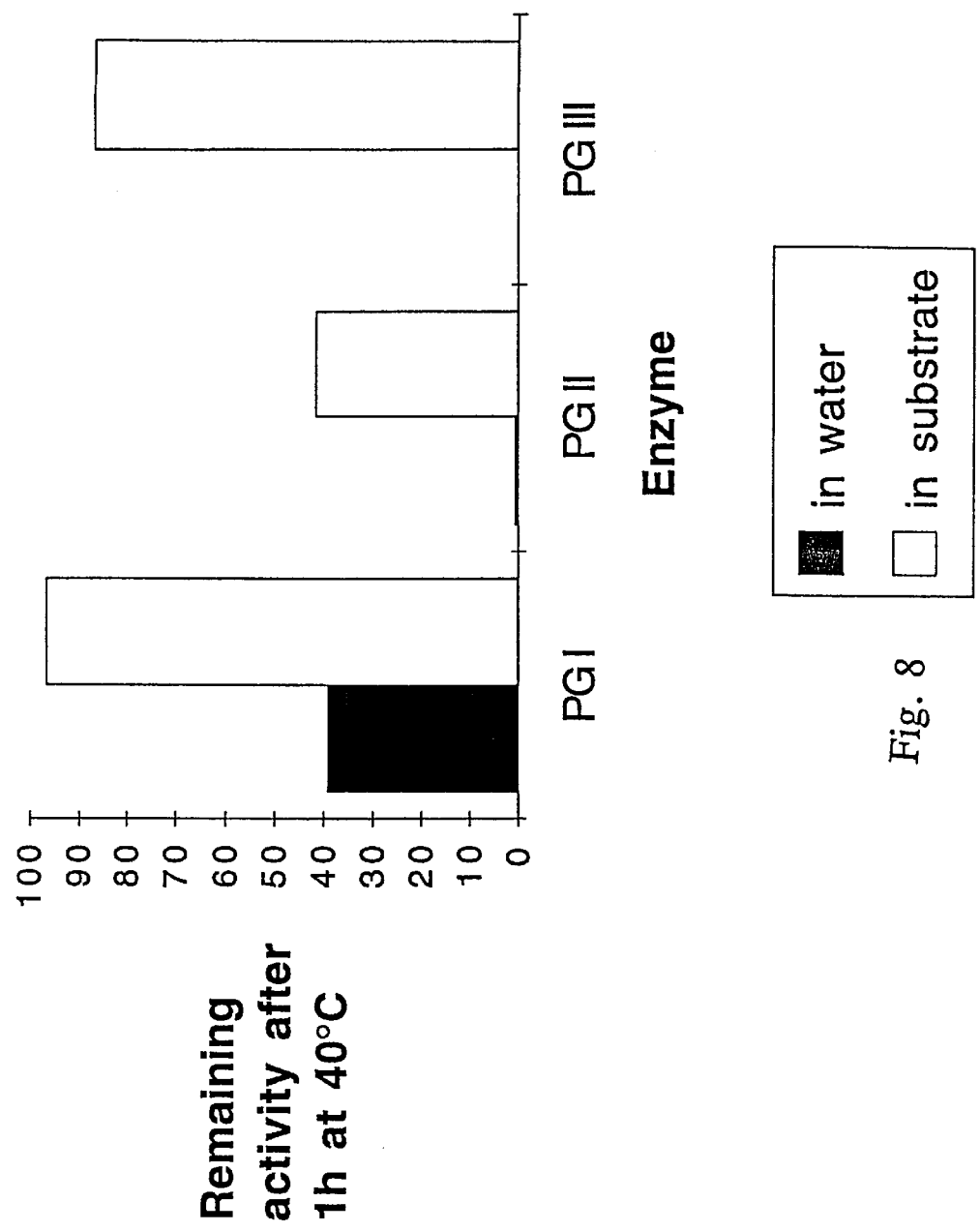

FIG. 1 is a restriction may of plasmid pYHD17,

FIG. 2 a restriction map of plasmid pHD 414,

FIG. 3a a silver stained SDS-PAGE gel (FIG. 3a) in which Lane 1 contains molecular weight makers (rabbit muscle phosphorylase B (94 kDa), bovine serum albumin (67 kDa), ovalbumin (43 kDa), bovine erythrocyte carbonic anhydrase (30 kDa), trypsin inhibitor (20.1 kDa), and lane 2 crude supernatant from A. aculeatus, lane 3 purified PG I, lane 4 purified PG II and lane 5 purified PG III, FIG. 3b a Coomassie stained IEF gel, in which Lane 1 contains isoelectric point markers (A: Amyloglycosidase pI 3.5; B: Soy bean trypsin inhibitor pI 4.55; C: Bovine carbonic anhydrase pI 5.85; D: Horse myoglobin (acidic band) pI 6.85; E: Horse myoglobin (basic band) pI 7.35; F: Lentil lectin acidic band pI 8.15; G: Lentil lectin middle band pI 8.45), Lane 2 crude culture supernatant from A. aculeatus, Lane 3 purified PG I, Lane 4 purified PG II and Lane 5 purified PG III, FIG. 4 the pH optimums for PG I, PG II and PG III measured in citrate/phosphate buffers. The optimal activity for each enzyme is defined as 100%, FIG. 5 the pH stability of PG I, PG II and PG III measured as the remaining activity after 1 h at different pH values compared to the activity of fresh enzyme (100%), FIG. 6 the temperature optimum for PG I and PG II. The activity at the optimal temperature is defined as 100%, FIG. 7 the temperature stability of PG I, PG II and PG III measured as the remaining activity after preincubation in water for 1 h at different temperatures compared to the activity of fresh enzyme (100%), and FIG. 8 the stabilisation with substrate determined as the remaining activity (compared to fresh enzyme) of PG I, PG II and PG III after preincubation for 1 hour at 40° C. in water and polygalacturonic acid, respectively.

The invention is described in further detail in the following examples which are not in any way intended to limit the scope of the invention as claimed.

MATERIALS AND METHODS

Donor Organism mRNA was isolated from *Aspergillus aculeatus*, CBS 101.43, grown in a soy-containing fermentation medium with agitation to ensure sufficient aeration. Mycelia were harvested after 3–5 days' growth, immediately frozen in liquid nitrogen and stored at −80° C.

Yeast Strains

The *Saccharomyces cerevisiae* strain used was yNG2 ino (MAT alpha, leu2, ura3–52, his4–539, pep4-delta 1, cir+) or JG169 (MATα; ura 3–52; leu 2–3, 112; his 3-D200; pep 4–113; prc1::HIS3; prb1::LEU2; cir+).

Construction of an Expression Plasmid

The commercially available plasmid pYES II (Invitrogen) was cut with SpeI, filled in with Klenow DNA polymerase+dNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by Ball exonuclease treatment followed by addition of a SphI linker. Finally, an EcoRI linker was added at position −10. After these modifications, the promoter is included in a SphI-EcoRI fragment. Its efficiency compared to the original promoter appears to be unaffected by the modifications. The resulting plasmid pYHD17 is shown in FIG. 1.

Preparation of RNase-Free Glassware, Tips and Solutions

All glassware used in RNA isolations was baked at +220° C. for at least 12 h. Eppendorf tubes, pipet tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of Total RNA

The total RNA was prepared by extraction with guanidinium thiocyanate followed by ultracentrifugation through a 5.7 M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4 M GuSCN, 0.5% Na-laurylsarcosine, 25 mM Na-citrate, pH 7.0, 0.1 M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7 M CsCl cushion (5.7 M CsCl, 0.1 M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25000 rpm, RT°, 24 h). After centrifugation the supernatant was carefully removed and the bottom of the tube containing the RNA pellet was cut off and rinsed with 70% EtOH. The total RNA pellet was transferred into an Eppendorf tube, suspended in 500 µl TE, pH 7.6 (if difficult, heat occasionally for 5 min at 65° C.), phenol extracted and precipitated with ethanol for 12 h at −20° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of Poly(A)$^+$RNA

The poly(A)$^{30}$RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1× column loading buffer (20 mM Tris-Cl, pH 7.6, 0.5 M NaCl, 1 mM EDTA, 0.1% SDS), loaded onto a DEPC-treated, plugged plastic column (Poly Prep Chromatography column, Bio Rad), and equilibrated with 20 ml 1× loading buffer. The total RNA was heated at 65° C. for 8 min., quenched on ice for 5 min, and after addition of 1 vol 2× column loading buffer to the RNA sample loaded onto the column. The eluate was collected and reloaded 2–3 times by heating the sample as above and quenching on ice prior to each loading. The oligo(dT) column was washed with 10 vols of 1× loading buffer, then with 3 vols of medium salt buffer (20 mM Tris-Cl, pH 7.6, 0.1 M NaCl, 1 mM EDTA, 0.1% SDS), followed by elution of the poly(A)$^+$ RNA with 3 vols of elution buffer (10 mM Tris-Cl, pH 7.6, 1 mM EDTA, 0.05% SDS) preheated to +65° C., by collecting 500 µl fractions. The $OD_{260}$ was read for each collected fraction, and the mRNA containing fractions were pooled and ethanol precipitated at −20° C. for 12 h. The poly(A)$^+$ RNA was collected by centrifugation, resuspended in DEPC-DIW and stored in 5–10 µg aliquots at −80° C.

Northern Blot Analysis

The poly(A)$^+$ RNAs (5 µg/sample) from various mycelia were electrophoresed in 1.2 agarose-2.2 M formaldehyde gels (Sambrook et al., 1989) and blotted to nylon membranes (Hybond-N, Amersham) with 10× SSC (Sambrook et al., 1989) as transfer buffer. Three random-primed (Feinberg & Vogelstein, 1983) $^{32}$P-labelled cDNA probes were used in individual hybridizations: 1) a 1.3 kb Not I-Spe I fragment for polygalacturonase I from *A. aculeatus* (described herein), 2) a 1.3 kb Not I-Spe I fragment encoding endo-glucanase I from *A. aculeatus* (described in DK 0419/92), and 3) a 1.2 kb Eag I fragment for galactanase I from *A. aculeatus* (described in WO 92/13945). Northern hybridizations were carried out in 5× SSC (Sambrook et al., 1989), 5× Denhardt's solution (Sambrook et al., 1989), 0.5% SDS (w/v) and 100 µg/ml denatured salmon sperm DNA with a probe concentration of approx. 2 ng/ml for 16 h at 65° C. followed by washed in 5× SSC at 65° C. (2×15 min), 2× SSC, 0.5% SDS (1×30 min), 0.2× SSC, 0.5% SDS (1×30 min), and 5× SSC (2×15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA Synthesis

First Strand Synthesis

Double-stranded cDNA was synthesized from 5 µg of *A. aculeatus* poly(A)+ RNA by the RNase H method (Gubler & Hoffman 1983, Sambrook et al., 1989) using the hair-pin modification. The poly(A)+RNA (5 µg in 5 µl of DEPC-treated water) was heated at 70° C. for 8 min., quenched on ice, and combined in a final volume of 50 µl with reverse transcriptase buffer (50 mM Tris-Cl, pH 8.3, 75 mM KCl, 3 mM MgCl2, 10 mM DTT, Bethesda Research Laboratories) containing 1 mM each dNTP (Pharmacia), 40 units of human placental ribonuclease inhibitor (RNasin, Promega), 10 µg of oligo(dT)$_{12-18}$ primer (Pharmacia) and 1000 units of SuperScript II RNase H- reverse transcriptase (Bethesda Research Laboratories). First-strand cDNA was synthesized by incubating the reaction mixture at 45° C. for 1 h.

Second Strand Synthesis

After synthesis 30 µl of 10 mM Tris-Cl, pH 7.5, 1 mM EDTA was added, and the mRNA:cDNA hybrids were ethanol precipitated for 12 h at −20° C. by addition of 40 µg glycogen carrier (Boehringer Mannheim) 0.2 vols 10 M NH$_4$Ac and 2.5 vols 96% EtOH. The hybrids were recovered by centrifugation, washed in 70% EtOH, air dried and resuspended in 250 µl of second strand buffer (20 mM Tris-Cl, pH 7.4, 90 mM KCl, 4.6 mM MgCl2, 10 mM (NH$_4$)$_2$SO$_4$, 16 µM βNAD$^+$) containing 100 µM each dNTP, 44 units of *E. coli* DNA polymerase I (Amersham), 6.25 units of RNase H (Bethesda Research Laboratories) and 10.5 units of *E. coli* DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung Bean Nuclease Treatment

The double-stranded (ds) cDNA was ethanol precipitated at −20° C. for 12 h by addition of 2 vols of 96% EtOH, 0.1 vol 3 M NaAc, pH 5.2, recovered by centrifugation, washed in 70% EtOH, dried (SpeedVac), and resuspended in 30 µl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 µl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-Ending with T4 DNA Polymerase

The ds cDNA was blunt-ended with T4 DNA polymerase in 50 µl of T4 DNA polymerase buffer (20 mM Tris-acetate, pH 7.9, 10 mM MgAc, 50 mM KAc, 1 mM DTT) containing 0.5 each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor Ligation and Size Selection

After the fill-in reaction the cDNA was ligated to non-palindromic BstX I adaptors (1 µg/µl, Invitrogen) in 30 µl of ligation buffer (50 mM Tris-Cl, pH 7.8, 10 mM MgCl2, 10 mM DTT, 1 mM ATP, 25 µg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of cDNA Libraries

The adapted, ds cDNA was recovered by centrifugation, washed in 70% EtOH and resuspended in 25 ml DIW. Prior to large-scale library ligation, four test ligations were carried out in 10 µl of ligation buffer (same as above) each containing 1 µl ds cDNA (reaction tubes #1–190 3), 2 units of T4 ligase (Invitrogen) and 50 ng (tube #1), 100 ng (tube #2) and 200 ng (tubes #3 and #4) Bst XI cleaved yeast expression vector either pYES 2.0 vector Invitrogen of yHD13). The ligation reactions were performed by incubation at +16° C. for 12 h, heated at 70° C. for 5 min, and 1 µl of each ligation electroporated (200 Ω, 2.5 kV, 25 µF) to 40 µl competent *E. coli* 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h, 50 µl plated on LB+ ampicillin plates (100 µg/ml) and grown at +37° C. for 12 h.

Using the optimal conditions a large-scale ligation was set up in 40 µl of ligation buffer containing 9 units of T4 ligase, and the reaction was incubated at +16° C. for 12 h. The ligation reaction was stopped by heating at 70° C. for 5 min, ethanol precipitated at −20° C. for 12 h, recovered by centrifugation and resuspended in 10 µl DIW. One µl aliquots were transformed into electrocompetent *E. coli* 1061 cells using the same electroporation conditions as above, and the transformed cells were titered and the library plated on LB+ ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 µl of −80° C. bacterial stock propagated overnight.

Construction of yeast libraries: To ensure that all the bacterial clones were tested in yeast, a number of yeast transformants 5 times larger than the number of bacterial clones in the original pools was set as the limit.

One µl aliquots of purified plasmid DNA (100 ng/µl) from individual pools were electroporated (200 Ω, 1.5 kV, 25 µF) into 40 µl competent *S. cerevisiae* JG 169 cells (OD600=1.5 in 500 ml YPD, washed twice in cold DIW, once in cold 1 M sorbitol, resuspended in 0.5 ml 1 M sorbitol, Becker & Guarante, 1991). After addition of 1 ml 1M cold sorbitol, 80 µl aliquots were plated on SC+glucose–uracil to give 250–400 c.f.u./plate and incubated at 30° C. for 3–5 days.

Construction of an Aspergillus expression vector: the vector pHD414 is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and relegation of the vector fragment. This plasmid was called pHD413. pHD413 was cut with StuI (positioned in the 5'end of the promoter) and PvuII (in the pUC vector), fractionated on gel and religated. The plasmid pHD 414 is shown in FIG. 2.

Media:

YPD: 10 g yeast extract, 20 g peptone, $H_2O$ to 810 ml. Autoclaved, 90 ml 20% glucose (sterile filtered) added.

10×Basal salt: 66.8 g yeast nitrogen base, 100 g succinic acid, 60 g NaOH, $H_2O$ and 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose added.

SC-H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition was YNB-1 agar, but without the agar.

Pectin overlayer gel: 1% agarose, 1% apple pectin (DE 35%) (purified from apple pectin manufactured by Obipektin AG) in 0.1 M citrate-phosphate buffer, pH 4.5. The gel was boiled and then cooled to 55° C. before the overlayer was poured onto agar plates.

Characterization of an Enzyme of the Invention:

SDS-PAGE Electrophoresis: SDS-PAGE electrophoresis was performed in a Mini-Leak 4 electrophoresis unit (Kem-En-Tec, Copenhagen) as a modified version of the Laemli procedure (Laemmli, 1970; Christgau et al., 1991). Briefly, the separation gel was cast with 12% acrylamide; 0.2% BIS acrylamide; 0.1% SDS; 0.375 M Tris pH 8.8; 0.04% APS (ammonium-persulphate) & 0.04% TEMED. After 6–15 hours of polymerization the stacking gel was cast with 4.5% w/w Acrylamide; 0.075% BIS-acrylamide; 0.1% SDS; 66.5 mM Tris pH 6.8; 0.4% w/w APS (ammonium persulphate) & 0.4% TEMED. The electrode chambers are filled with running buffer: 25 mM Tris-base; 0.192 M glycine & 0.05% SDS, whereafter the samples containing sample buffer are loaded, and the gel is run at 2–4 mA/gel for over-night running and 10–30 mA/gel for fast running. The gel is subsequently removed and stained by either commassie or silver staining.

Isoelectric focusing: Isoelectric focusing is carried out on Ampholine PAG plates pH 3.5–9.5 (Pharmacia, Upsala) on a Multiphor electrophoresis unit according to the manufactures instructions. After electrophoresis the gel is either commassie stained or silver stained.

Commassie and silver staining: The gel is carefully removed from the glass plates and incubated on a slowly rotating shaking table in approximately 100 ml of the following solutions:

Coomassie Staining:
1) 30 min in 40% v/v ethanol; 5% v/v acetic acid
2) 30 min in 40% v/v ethanol; 5% v/v acetic acid+0.1% Coomassie R250
3) Destaining in 30 min in 40% v/v ethanol; 5% v/v acetic acid until background is sufficiently reduced.
4) Finally the gel is incubated in preserving solution: 5% v/v acetic acid ; 10% v/v ethanol; 5% v/v glycerol and air dried between two sheets of cellophane membrane.

Silver Staining:
1) 30 min in 40% v/v ethanol; 5% v/v acetic acid
2) 20 min in 10% v/v ethanol; 5% v/v acetic acid
3) 20 min in 0.0057% w/v APS (0.25 mM)
4) 60 min in 0.1% w/v $AgNO_3$
5) For development, the gel is dipped in developer: 0.015% formaldehyde; 2% w/v $Na_2CO_3$ for 30–60 sec. Then the gel is incubated in a second round of developer until satisfactory staining of the proteins has been achieved (5–15 min.). Finally the gel is incubated in preserving solution: 5% v/v acetic acid; 10% v/v ethanol; 5% v/v glycerol and air dried between two sheets of cellophane membrane.

Standard incubations: For standard incubations with the enzyme, incubations are carried out in Eppendorf tubes comprising 1 ml of substrate. The substrate is polygalacturonic acid from Sigma. When the enzyme is added incubation is carried out for 15 min at 30° C. (if not otherwise specified) and the enzyme is inactivated at 95° C. for 20 minutes. Enzyme incubations are carried out in triplicate. A blank is produced in which enzyme is added but inactivated immediately.

The enzyme activity is measured by determining the amount of reducing sugars released by the enzyme during the 15 minutes of incubation compared to the blank. Reducing sugars are determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Galacturonic acid is used as a standard.

pH optimum is measured as described above in 0.1 M citric acid/tri sodium phosphate buffers of varying pH.

pH stability is measured by leaving the enzyme for 1 hour in 0.1 M citric acid/tri sodium phosphate buffers of varying pH before the enzyme is used for incubation at the optimal pH.

Temperature optimum is measured by incubating the enzyme at varying temperatures for 15 minutes at the optical pH.

Temperature stability is measured by leaving the enzyme, diluted in water, at various temperatures for 1 and 2 hours before incubation at 30° C. at optimal pH.

Substrate stabilisation is measured by leaving the enzyme in the presence of substrate and buffer of optimal pH for 1 hour at 40° C. for 1 hour before incubation at 30° C. at optimal pH.

Km and specific activity are measured by carrying out incubations at substrate concentrations (S) ranging from 0.025 to 1.5% polygalacturonic acid, measure the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

HPLC-SEC: Enzyme incubations for HPLC-SEC analyses are carried out by adding enzyme to 1 ml of 1% pectic substrate in 0.1 M acetate buffer having a suitable pH and incubate 0, 1, 2, 4 and 24 hours before the enzyme is inactivated. 25 µl of each sample are injected to SEC columns (TSK G4000PW, TSK G3000PW, TSK G2500PW columns connected in a row) and eluted with 0.4 M acetate buffer pH 3.0 at 0.8 ml/min supplied by a Dionex pump. Eluting carbohydrates are detected by a refractive index detector (Shimadzu) and the chromatograms are processed by Dionex software. The SEC degradation profile of polygalacturonases has been obtained for four different substrates: polygalacturonic acid (Sigma), 35% DE apple pectin purified from apple pectin manufactured by Obipektin AG, 75% DE apple pectin purified from apple pectin manufactured by Herbstreith KG Perkin Fabrik, and saponified Modified Hairy Regions (MHR-S) obtained from apples by the procedure described by Schols et al, 1990. Dextrans (from SERVA) are used as molecular weight standards.

EXAMPLES

Example 1

Cloning and Characterization of DNA Encoding PG I, PG II, and PG III

A library from *A. aculeatus* consisting of approx. $1.5 \times 10^6$ individual clones in 150 pools was constructed.

DNA was isolated from 20 individual clones from the library and subjected to analysis for cDNA insertion. The insertion frequency was found to be <90% and the average insert size was approximately 1400 bp.

DNA from some of the pools was transformed into yeast, and 50–100 plates containing 200–500 yeast colonies were obtained from each pool. After 4 or 5 days of growth, the agar plates were replica plated onto several sets of agar plates. One set of plates was then incubated for 2–4 days at 30° C. and overlayered with a pectin indicator gel for detection of pectinolytic activity. After incubation overnight at 40° C., enzyme reactions were visualised with MTAB (mixed alkyltrimethylammonium bromide). 10–15 ml of a 1% solution of MTAB was poured onto the overlayer and removed after 1–2 hours. Polygalacturonase-positive colonies were identified on the plates with the pectin overlayer as colonies with colourless clearing zones on an opaque (white) background.

Cells from enzyme-positive colonies were spread for single colony isolation on agar, and an enzyme-producing single colony was selected for each of the polygalacturonase-producing colonies identified.

Each of the polygalacturonase-producing colonies was inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9 M sorbitol, 0.1 M EDTA, pH 7.5. The pellet was transferred to an Eppendorf tube, and spun for 30 seconds at full speed. The cells were resuspended in 0.4 ml 0.9 M sorbitol, 0.1 M EDTA, 14 mM β-mercaptoethanol. 100 µl 2 mg/ml Zymolase was added, and the suspension was incubated at 37° C. for 30 minutes and spun for 30 seconds. The pellet (spheroplasts) was resuspended in 0.4 ml TE. 90 µl of (1.5 ml 0.5 M EDTA pH 8.0, 0.6 ml 2 M Tris-Cl pH 8.0, 0.6 ml 10% SDS) was added, and the suspension was incubated at 65° C. for 30 minutes. 80 µl 5 M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% ETOH, spun for 30 seconds and dried at room temperature. The pellet was resuspended in 50 µl TE and spun for 15 minutes. The supernatant was transferred to a fresh tube. 2.5 µl 10 mg/ml RNase was added, followed by incubation at 37° C. for 30 minutes and addition of 500 µl isopropanol with gentle mixing. The mixture was spun for 30 seconds, and the supernatant was removed. The pellet was rinsed with cold 96% EtOH and dried at room temperature. The DNA was dissolved in 50 µl water to a final concentration of approximately 100 µl/ml.

The DNA was transformed into *E. coli* by standard procedures. Two *E. coli* colonies were isolated from each of the transformations and analysed with the restriction enzymes HindIII and XbaI which excised the DNA insert. DNA from one of these clones was retransformed into yeast strain JG169.

The DNA sequences of several of the positive clones were partially determined. The partial DNA sequences of three distinct polygalacturonases are shown in claims 3, 5 and 6.

Example 2

Expression of PG I, PG II and PG III

In order to express the genes in Aspergillus, cDNA is isolated from one or more representatives of each family by digestion with HindIII/XbaI, sized fractionation on a gel and purification and subsequently ligated to HindIII/XbaI digested pHD414, resulting in the plasmids pAPGTypeI, pAPGTypeII, pAPGTypeIII. After amplification in *E. coli,* the plasmids are transformed into *A. oryzae* or *A. niger* according to the general procedure described below.

Transforamtion of *Aspergillus oryzae* or *Aspergillus niger* (General Procedure)

100 ml of YPD (Sherman et al., Methods in Yeast Genetics, Cold Spring Harbor Laboratory, 1981) is inoculated with spores of *A. oryzae* or *A. niger* and incubated with shaking at 37° C. for about 2 days. The mycelium is harvested by filtration through miracloth and washed with 200 ml of 0.6 M $MgSO_4$. The mycelium is suspended in 15 ml of 1.2 M $MgSO_4$. 10 mM $NaH_2PO_4$, pH=5.8. The suspension is cooled on ice and 1 ml of buffer containing 120 mg of Novozym® 234 , batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6 M sorbitol, 100 mM Tris-HCl, pH=7.0. Centrifugation is performed for 15 minutes at 100 g and the protoplasts are collected from the top of the $MgSO_4$ cushion. 2 volumes of STC (1.2 M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC. 100 µl of protoplast suspension is mixed with 5–25 µg of the appropriate DNA in 10 µl of STC. Protoplasts are mixed with p3SR2 (an *A. nidulans* amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on the appropriate plates. Protoplasts are spread on minimal plates (Cove Biochem. Biophys. Acta 113 (1966) 51–56) containing 1.0 M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* Transformants

Each of the transformants were inoculated on FG-4 agar in the centre of a Petri dish. After 5 days of incubation at 30° C., 4 mm diameter plugs were removed by means of a corkscrew. The plugs were embedded in pectin overlayer gel and incubated overnight at 30° C. The polygalacturonase activity was visualized as described above. The best transformants had a clearing zone significantly larger than the *A. oryzae* background. This demonstrates efficient expression of polygalacturonase I, I and III in *A. oryzae*.

Fed Batch Fermentation

Subsequently, PG I, PG II and PG III, respectively, were produced by fed batch fermentation of *A. oryzae* expressing the enzymes. The medium was used for the fermentation comprised maltodextrin as a carbon source, urea as a nitrogen source and yeast extract.

The fed batch fermentation were performed by inoculating a shake flask culture of the *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The fed batch cultivation was continued for 4 days after which the enzyme could be recovered.

Example 3

Characterization of PG I, PG II and PG III

Purification of PG I and PG II

The culture supernatant from fermentation of *Aspergillus oryzae* or *A. niger* expressing the recombinant enzyme was centrifuged at 5000 xg and filtered through a 0.2 μm filter to remove the mycelia. 35–50 ml of the filtered supernatant were ultrafiltrated in a Filtron ultracette or Amicon ultrafiltration device with a 10 kDa membrane to achieve 10 fold concentration. This concentrate was diluted 100 times in 50 mM Tris pH 8.0 in two successive rounds of ultrafiltration in the same device. This ultrafiltratred sample was loaded at 2 ml/min on a Pharmacia HR16/10 Fast Flow Q Sepharose anion exchanger equilibrated in 50 mM Tris pH 8.0. After the sample has been applied, the column was washed with two column volumes 50 mM Tris pH 8.0, and bound proteins were eluted with a linear increasing NaCl gradient from 0 to 0.6 M NaCl in 50 mM Tris pH 8.0.

Polygalacturonase I eluted at approximately 0.30–0.35 M NaCl, and fractions containing polygalacturonase activity were pooled and concentrated by ultrafiltration. Polygalacturonase I in this fraction was found not to be completely pure. Accordingly, the polygalacturonase containing fractions were concentrated by ultrafiltration in an Amicon ultrafiltration device with a 10 kDa membrane to achieve a 10 fold concentration. The resulting concentrate was diluted 100 times in 20 mM citrate pH 3.0 in two successive rounds of ultrafiltration in the same device. This ultrafiltrated sample was loaded at 1 ml/min. on a Pharmacia HR 10/20 Fast Flow S Sepharose cation exchanger equilibrated in 20 mM citrate pH 3.0. After the sample had been applied the column was washed with two column volumes 20 mM citrate pH 3.0 and bound proteins were eluted with a linear increasing NaCl gradient from 0 to 0.4 M NaCl in 50 mM Tris pH 8.0. Polygalacturonase I eluted at approximately 0.2 M NaCl. Polygalacturonase I in this fraction is more than 99% pure.

Polygalacturonase II elutes at approximately 0.55 M NaCl from the FF-Q anion exchange column. Fractions containing polygalacturonase activity were pooled and concentrated by ultrafiltration.

Purification of Polygalacturonase III

The culture supernatent from fermentation of *Aspergillus oryzae* of *A. niger* expressing the recombinant enzyme was centrifuged at 5,000 xg for 20 min and filtered through a 0.2 μm filter to remove the mycelia. 35–50 ml of the filtered supernatent were ultrafiltrated in a Filtron ultracette or Amicon ultrafiltration device with a 10 kDa membrane to achieve 10 fold concentration. This concentrate was diluted 100 times in 20 mM MES (2[N-Morpholino]-ethanesulfonic acid) pH 6.5 in two successive rounds of ultrafiltration in the same device. This ultrafiltrated sample was loaded at 2 ml/min on a Pharmacia HR 16/10 Fast Flow Q Sepharose anion exchanger equilibrated in 20 mM MES pH 6.5. After the sample had been applied, the column was washed with two column volumes 20 mM MES pH 6.5, and bound proteins were eluted with a linear increasing NaCl gradient from 0 to 1 M NaCl in 20 mM MES pH 6.5. PGI eluted at approximately 0.7–0.8 M NaCl, and fractions containing PG activity were pooled and concentrated by ultrafiltration. PG III in this fraction was purified to more than 99% homogeneity.

The purified polygalacturonases I, II and III have been characterized with respect to molecular weight, isoelectric point, pH optimum, pH stability, temperature optimum and temperature stability, substrate stabilization, buffer influence, $K_m$ and specific activity. Furthermore the degradation pattern of the enzymes on different pectic substrates has been investigated by HPLC Size Exclusion Chromatography.

The molecular characterization of polygalacturonase II is illustrated in FIG. 3. FIG. 3a illustrates the result of a silver stained SDS-PAGE gel. FIG. 3b illustrates the result of a Coomassie stained IEF gel. PG I has a molecular weight about of 43.5 kDa (as estimated from the SDS-PAGE gel) and a pI of about 4.7. PG II has a molecular weight of about 62.0 kD, and a pI below 3.0. PG III has a molecular weight of about 56.5 kDa and a pI of about 4.25. The molecular data are summarized in the table below:

|        | MW (kDa) | pI   |
|--------|----------|------|
| PG I   | 43.5     | 4.7  |
| PG II  | 62.0     | <3.0 |
| PG III | 56.5     | 4.25 |

The pH optimum, pH stability, temperature optimum and temperature stability of the purified PG I, PG II and PG III were determined as described above and the results are apparent from FIGS. 4 to 7, respectively. It is evident that PG I has a very broad pH optimum range and a remarkable stability for all pH values tested and a relatively higher temperature stability than PG II and PG III.

The stability of PG I, PG II and PG III in water with and without substrate was determined. From FIG. 8 it is evident that PG II and PG III show an unusual stability profile in that they are stable substantially only in the presence of substrate.

The Km and specific gravity for PG I, PG II and PG III were determined as described under Material and Methods. The standard deviation on 1/Vmax and Km/Vmax obtained from the linear regression analysis were used to calculate the intervals shown in the following table:

| Enzyme | KM<br>% polygalacturonic<br>acid | Specific<br>activity<br>μmol/min/mg | r^2 |
|---|---|---|---|
| PG I | 0.069–0.175 | 160–181 | 0.98 |
| PG II | 0.159–0.280 | 1500–1695 | 0.98 |
| PG III | 0.126–0.385 | 146–205 | 0.88 |

It is seen that PG II has approximately 10 times higher specific activity than PG I and PG III.

The degradation pattern obtained from reaction with PG I, PG II and PG III of the invention, respectively, was determined by a HPLC-SEC analysis performed as described in the Materials and Methods section above. For this purpose PG I was added to 1 ml of the substrate in an amount of 10 μg and PG II was added in an amount of 9 μg and the PG III in the amount of 6.3 μg. The pH of the substrate containing buffer was 5.0 and 4.0 and 4.0, for PG I, PG II and PG III respectively.

It was observed that PG I, PG II and PG III liberate monomers and dimers indicating that a trimer is the smallest substrate to be degraded. In this respect, PG II liberates much more monomer and dimer than PG I and PG III and is, in fact, capable of almost total degradation of polygalacturonic acid liberating substantial amounts of galacturonic acid and dimers of galacturonic acid. All enzymes have an endo mode of action although PG II is more "exo-like" than PG I and PG III. 35% DE pectin is degraded to some extent whereas the degradation of 75% DE pectin is much more limited, although some mono and dimer are released. PG II has the highest esterified pectin. The mean molecular weight of the polymeric 75% DE pectin is reduced seven fold by the action of PG II compared to four fold for PG I. PG II can be used for partial degradation of highly esterified pectins, lowering the viscosity, but leaving most of the pectin as polymeric substance. From MHR-5 also a small amount of monomer, dimer and higher oligomers are released.

REFERENCES

Plastow et al., *Symbiosis* 2, 1986, pp. 115–122

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74: 5463–5467.

Christgau, S., et al., 1991, "Pancreatic β-cells express two autoantigenic forms of glutamic acid decarboxylase, a 65 kDa hydrophilic form and a 64 kDa amphiphilic form which can be both membrane-bound and soluble.". J. Biol. Chem., 266, p. 21157–212664.

Laemmli, U. K., 1970, "Cleavage of structural proteins during the assembly of the head of bacteriophage T4"., Nature, 227, p. 680–685.

Schols, H. A. et al., Structural features of Hairy Regions of Pectins isolated from Apple Juice produced by the Liquefaction Process, Carbohydrate Research, 206, pp. 117–129, 1990.

Bussink et al., Expression and sequence comparison of the *Aspergillus niger* and *Aspergillus tubigensis* genes encoding polygalacturonase II, Curr Genet (1991) 19: 467–474.

Bussink et al., Molecular cloning, nucleotide sequence and expression of the gne encoding prepropolygalacturonaseII of *Aspergillus niger*, FEBS Letters (1990), vol. 273, p. 127–130.

Bussink et al., The polygalaturonases of *Aspergillus niger* are encoded by a family of diverged genes, Eur. J. Biochem. 208, 83–90 (1992).

Behere et al., Separation and limited characterization of three polygalacturonases of *Aspergillus niger*, Enzymee Microb. Technol., 1993, vol. 15, February, p. 158–161.

Keon J. and Waksman G., Common Amino Acid Domain among Endopolygalacturonases of Ascomycete Fungi, Applied and Environmental Microbiology, August 1990, Vol. 56, No. 8, p. 2522–2528.

Lourdes et al., Pectinase production by *Neurospora crassa*: purification and biochemical characterization of extracellular polygalacturonase activity, Jour. of Gen Microbiology (1991), 137, 18151–1823.

Siessere et al., Extracellular polygalacturonases from *Penicillium frequentans*: separation and regulatory aspects, Jour. of Gen. Microbiology (1992), 138, 1801–1805.

Kester H. C. M. and Visser J., Purification and Characterization of Polygalacturonases Produced by the Hyphal Fungus *Aspergillus niger*, Biotechn. and applied Biochemistry 12, 150–160 (1990).

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CCAACAATGC ACCTTAACAC                                                        20

(2) INFORMATION FOR SEQ ID NO:2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:2:

CACCCTACTC GTCTCGCTCG                                                        20

(2) INFORMATION FOR SEQ ID NO:3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:3:

CCCTCGGGCG CGCGAGCGTC                                                        20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:4:

CTCGCCAGCC CAGCCCCACC                                                        20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

AGCAATCACG GCCCCGCCCA                                                        20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

```
CGGCCGAGGA GATCGCGAAG                                                    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCGACGACCT GCACGTTCTC                                                    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGGATCGAAC GGCGCCTCGT                                                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGGCCAGCAA GTCAAGACCT                                                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTGCTCGACC ATGTGTTGTG                                                    20

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

AATGTGCCGT TCCGTGCG                                                      18
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTTCTCTCTT TCGATTCTGT                                                20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TGATCAGACA CTCATTCCTT                                                20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CCTTTATTCA CTCTTTATCA                                                20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CGATTCTGTT TGACCAGAAT                                                20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CCATCATGCA CTCCTTCCAG                                                20

(2) INFORMATION FOR SEQ ID NO:17:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CTTCTCGGCC TGGCGCCTGT                                           20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CGGCTCCGTC GTCTCGGCCG                                           20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CTCCTACTGC GTCTCGTGTC                                           20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TCCGACCTTG TGAAGAATCC                                           20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TCTTCTACCT GCACTTTCAC                                           20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:22:

CTCTGCCAGC GAGGCTAGCG                                                       20

(2) INFORMATION FOR SEQ ID NO:23:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:23:

AAACGTCTTC TTCGTGCTCC AACGTC                                                26

(2) INFORMATION FOR SEQ ID NO:24:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:24:

ACATTCACAC TCCCTCATAA                                                       20

(2) INFORMATION FOR SEQ ID NO:25:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:25:

AATCTCTTTA CACCTGCTCA                                                       20

(2) INFORMATION FOR SEQ ID NO:26:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:26:

CCCTCTGTCA TTCTTTATTC                                                       20

(2) INFORMATION FOR SEQ ID NO:27:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:27:

-continued

```
TTTCCTACCA ACAAAAATGG                                               20

(2) INFORMATION FOR SEQ ID NO:28:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:28:

TTCGTCAGCT TGCATTGGCC                                               20

(2) INFORMATION FOR SEQ ID NO:29:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:29:

TGCGGACTGC TGGCAGCAGT                                               20

(2) INFORMATION FOR SEQ ID NO:30:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:30:

GGCCGTCCAG GCAGCCCCCG                                               20

(2) INFORMATION FOR SEQ ID NO:31:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:31:

CGGAACCGGC TGATCCGAAG                                               20

(2) INFORMATION FOR SEQ ID NO:32:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:32:

GGTGACTGAA TCGCCG                                                   16

(2) INFORMATION FOR SEQ ID NO:33:
```

(i) SEQUENCE CHARACTERISTICS:
    (A) LENGTH: 257 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:33:

```
ACCAAGACAA CCCGAAGCTT GAACCCTCTT GGCCCAAATC CAACAATGCA CCTTAACACC     60
ACCCTACTCG TCTCGCTCGC CCTCGGGCGC GCGAGCGTCC TCGCCAGCCC AGCCCCACCA    120
GCAATCACGG CCCCGCCCAC GGCCGAGGAG ATCGCGAAGG CGACGACCTG CACGTTCTCC    180
GGATCGAACG GCGCCTCGTC GGCCAGCAAG TCAAGACCTG TGCTCGACCA TGTGTTGTGA    240
ATGTGCCGTT CCGTGCG                                                   257
```

(2) INFORMATION FOR SEQ ID NO:34:

(i) SEQUENCE CHARACTERISTICS:
    (A) LENGTH: 864 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:34:

```
AAGTCTCGCG CGCACAGCCT GACCAACTCG GTGATTCAGC GGCTGAAGAT CGTCAACTCG     60
CCGGTGCAGG TTTTCACGTT GCGGGGTCGG ATTATCTGAC CCTCAAGGAT ATCACGATCG    120
ACAACTCGGA CGGCGACGAC AATGGCGGGC ATAATACCGA TGCGTTTGAT ATCGGCACGA    180
GCACGTATGT CACGATCTCG GGCGCCACGG TGTATAATCA GGATGATTTG CGTGGGCTGT    240
GTAATTCGGG GGAGAATATC TACTTCTCGG GCGGCCTACT GCTCCGGTGG ACACGGCTTG    300
TCCATTGGTT CGGTGGGCGG ACGCAGTGAT AATACGGTTA AGAACGTGAC GTTTGTGGAT    360
TCGACGATCA TTAACTCAGA TAATCGGTCC GCAATCAAAA CCAACATCGA CACCACCGGC    420
TCCGTGTCCG ACGTCACCTA CAAGGACATC ACGCTCACCT CCATCGCCAA GTACGGGATC    480
GTGGTGCAGC AGAACTACGG CGACACGTCA TCGACGCCCA CGACGGGGGT GCCGATCACG    540
GACTTTGTGC TGGACAACGT GCACGGCTCG GTGGTCAGCT CGGGGACCAA CATCCTCATC    600
TCGTGCGGGG TCGGGCAGTT GTTCGGATTG GAGTGGACGG ATGTGAGTGT CAGTGGGGGG    660
AAGACGAGTT CCAAGTGTAC GAATGTGCCG AGTGGGCTA GTTGTTGATT CTCTGGTTGT    720
TTGTGGTTGA GAGGGGAGG GGGGGTGATT TCTCAAGCTG GAAGGGGTTC TTCGAGCTTA    780
GGAGGTCTCA GGCTTAGTTT GGAGAGCGGA ACGGGTCTCT TGACTACTTA GGTTGCTCTT    840
GTTTGAATGG GAAAAAAAAA AAAA                                           864
```

(2) INFORMATION FOR SEQ ID NO:35:

(i) SEQUENCE CHARACTERISTICS:
    (A) LENGTH: 426 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:35:

```
GTTCTCTCTT TCGATTCTGT TGATCAGACA CTCATTCCTT CCTTTATTCA CTCTTTATCA     60
```

-continued

```
CGATTCTGTT TGACCAGAAT CCATCATGCA CTCCTTCCAG CTTCTCGGCC TGGCGCCTGT    120

CGGCTCCGTC GTCTCGGCCG CTCCTACTGC GTCTCGTGTC TCCGACCTTG TGAAGAATCC    180

TCTTCTACCT GCACTTTCAC CTCTGCCAGC GAGGCTAGCG AAACGTCTTC TTCGTGCTCC    240

AACGTGGTCC TCAGCAACAT GAGGTGCCCG CCGGAGAGAC ACTTGACCTG TCGACAGCGC    300

TGACGGGTGC CACCATCACT TTTGAGGGTA CCACCAGCTT CGGCTACGAG GAATGGGATG    360

GTCTCTTATC CGTTTCGGCG GAACGAGCAT CACCATCACC CAGTCTGACG GTGCTGTCAT    420

TGACGG                                                              426
```

(2) INFORMATION FOR SEQ ID NO:36:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
AAAGACATTC ACACTCCCTC ATAAAATCTC TTTACACCTG CTCACCCTCT GTCATTCTTT     60

ATTCTTTCCT ACCAACAAAA ATGGTTCGTC AGCTTGCATT GGCCTGCGGA CTGCTGGCAG    120

CAGTGGCCGT CCAGGCAGCC CCCGCGGAAC CGGCTGATCC GAAGGGTGAC TGAAGCGCCG    180

GACGCCAGCC TCCTCCACAA GCGAGCCACC ACTTGCACCT TCTAGGCTCT GAGGGAGCTT    240

CAA                                                                 243
```

(2) INFORMATION FOR SEQ ID NO:37:

(i) SEQUENCE CHARACTERISTICS:
        (A) LENGTH: 349 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

```
CCATATCACT GGCGTTCCCA TCACGGATTT CACCCTCGAG AACGTGATTG GTACTTGTGC     60

GGACGACGAC TGCACCGAGG TTTACATTGC GTGTGGTAGT GGCGCCTGCT CGAACTGGAG    120

CTGGTCCAGC AGTGAAGTGT CACGGGCGGC AAGGTCGAGC TCCAAGTGCC TGAATGTCTT    180

CCGGATAAGC TGCGACTTGT AGGGGACTTT GCCGCTGGAG TCGGCTGGAC TTCCCAGGGA    240

ACTGTTCTAT CTCGCTATGG CTGTGGACGT ACCAGGACAT GCCACCAAGC GCCTAGTCAA    300

CATATCTATC TTCTGCCAAA TGAATACTAA TTTCCAAAAA AAAAAAAA                 349
```

What is claimed is:

1. An isolated and purified DNA sequence which encodes an enzyme exhibiting polygalacturonase activity and which DNA sequence hybridizes to a DNA sequence comprising

ACCAAGACAACCCGAAGCTTGAACCCTCTTGGCC (SEQ ID NO: 33)

CAAATCCAACAATGCACCTTAACACCACCCTACT

CGTCTCGCTCGCCCTCGGGCGCGCGAGCGTCCTC

GCCAGCCCAGCCCCACCAGCAATCACGGCCCCGC

CCACGGCCGAGGAGATCGCGAAGGCGACGACCTG

CACGTTCTCCGGATCGAACGGCGCCTCGTCGGCC

AGCAAGTCAAGACCTGTGCTCGACCATGTGTTGT

GAATGTGCCGTTCCGTGCG or

AAGTCTCGCGCGCACAGCCTGACCAACTCGGTGA (SEQ ID NO: 34)

TTCAGCGGCTGAAGATCGTCAACTCGCCGGTGCA

-continued

GGTTTTCACGTTGCGGGGTCGGATTATCTGACCC

TCAAGGATATCACGATCGACAACTCGGACGGCGA

CGACAATGCGGGCATAATACCGATGCGTTTGAT

ATCGGCACGAGCACGTATGTCACGATCTCGGGCG

CCACGGTGTATAATCAGGATGATTTGCGTGGGCT

GTGTAATTCGGGGGAGAATATCTACTTCTCGGGC

GGCCTACTGCTCCGGTGGACACGGCTTGTCCATT

GGTTCGGTGGGCGGACGCAGTGATAATACGGTTA

AGAACGTGACGTTTGTGGATTCGACGATCATTAA

CTCAGATAATCGGTCCGCAATCAAAACCAACATC

GACACCACCGGCTCCGTGTCCGACGTCACCTACA

AGGACATCACGCTCACCTCCATCGCCAAGTACGG

GATCGTGGTGCAGCAGAACTACGGCGACACGTCA

TCGACGCCCACGACGGGGGTGCCGATCACGGACT

TTGTGCTGGACAACGTGCACGGCTCGGTGGTCAG

CTCGGGGACCAACATCCTCATCTCGTGCGGGGTC

GGGCAGTTGTTCGGATTGGAGTGGACGGATGTGA

GTGTCAGTGGGGGAAGACGAGTTCCAAGTGTAC

GAATGTGCCGAGTGGGGCTAGTTGTTGATTCTCT

GGTTGTTTGTGGTTGAGAGGGGGAGGGGGGTGA

TTTCTCAAGCTGGAAGGGGTTCTTCGAGCTTAGG

AGGTCTCAGGCTTAGTTTGGAGAGCGGAACGGGT

CTCTTGACTACTTAGGTTGCTCTTGTTTGAATGG

GAAAAAAAAAAAAA under the following conditions: hybridizing in 5× SSC, 5× Denhardt's solution, 50 mM sodium phosphate, pH 6.8 and 50 ug denatured sonicated calf thymus DNA for 18 hrs at about 40 C. followed by washing three times in 2× SSC, 0.2% SDS at 40 C. for 30 minutes.

2. The DNA sequence according to claim 1, in which said DNA sequence is isolated from a DNA library of Aspergillus.

3. The DNA sequence according to claim 1, in which said DNA sequence is isolated from a DNA library of *Aspergillus aculeatus*.

4. The DNA sequence according to claim 1, in which said DNA sequence is isolated from a DNA library of *Aspergillus aculeatus*, CBS 101.43.

5. A recombinant expression vector comprising the DNA sequence according to claim 1.

6. A cell comprising the recombinant expression vector according to claim 5.

7. The cell according to claim 6 in which said cell is a eucaryotic cell.

8. The cell according to claim 6, in which said cell is a fungal cell.

9. The cell according to claim 6, in which said cell is a yeast cell or filamentous fungal cell.

10. The cell according to claim 6, in which said cell belongs to a strain of Aspergillus.

11. The cell according to claim 6, in which said cell belongs to a strain of *Aspergillus niger* or *Aspergillus oryzae*.

12. A method of producing an enzyme exhibiting polygalacturonase activity comprising culturing the cell of claim 6 under conditions permitting the production of the enzyme and recovering the enzyme from the culture.

13. A purified and isolated DNA sequence encoding a polygalacturonase having the identifying characteristics of a polygalacturonase enzyme which is encoded by a DNA sequence comprising

ACCAAGACAACCCGAAGCTTGAACCCTCTTGGCC (SEQ ID NO: 33)

CAAATCCAACAATGCACCTTAACACCACCCTAC

TCGTCTCGCTCGCCCTCGGGCGCGCGAGCGTCC

TCGCCAGCCCAGCCCCACCAGCAATCACGGCCC

CGCCCACGGCCGAGGAGATCGCGAAGGCGACGA

CCTGCACGTTCTCCGGATCGAACGGCGCCTCGT

CGGCCAGCAAGTCAAGACCTGTGCTCGACCATG

TGTTGTGAATGTGCCGTTCCGTGCG or

AAGTCTCGCGCGCACAGCCTGACCAACTCGGTGA (SEQ ID NO: 34)

TTCAGCGGCTGAAGATCGTCAACTCGCCGGTGCA

GGTTTTCACGTTGCGGGGTCGGATTATCTGACCC

TCAAGGATATCACGATCGACAACTCGGACGGCGA

CGACAATGCGGGCATAATACCGATGCGTTTGAT

ATCGGCACGAGCACGTATGTCACGATCTCGGGCG

CCACGGTGTATAATCAGGATGATTTGCGTGGGCT

GTGTAATTCGGGGGAGAATATCTACTTCTCGGGC

GGCCTACTGCTCCGGTGGACACGGCTTGTCCATT

GGTTCGGTGGGCGGACGCAGTGATAATACGGTTA

AGAACGTGACGTTTGTGGATTCGACGATCATTAA

CTCAGATAATCGGTCCGCAATCAAAACCAACATC

GACACCACCGGCTCCGTGTCCGACGTCACCTACA

AGGACATCACGCTCACCTCCATCGCCAAGTACGG

GATCGTGGTGCAGCAGAACTACGGCGACACGTCA

TCGACGCCCACGACGGGGGTGCCGATCACGGACT

TTGTGCTGGACAACGTGCACGGCTCGGTGGTCAG

CTCGGGGACCAACATCCTCATCTCGTGCGGGGTC

GGGCAGTTGTTCGGATTGGAGTGGACGGATGTGA

GTGTCAGTGGGGGAAGACGAGTTCCAAGTGTAC

GAATGTGCCGAGTGGGGCTAGTTGTTGATTCTCT

GGTTGTTTGTGGTTGAGAGGGGGAGGGGGGTGA

TTTCTCAAGCTGGAAGGGGTTCTTCGAGCTTAGG

AGGTCTCAGGCTTAGTTTGGAGAGCGGAACGGGT

CTCTTGACTACTTAGGTTGCTCTTGTTTGAATGG

GAAAAAAAAAAAAA said identifying characteristics of said polygalacturonase comprising: (a) a pH optimum above 5.5; (b) a temperature optimum between 40–60° C.; and (c) retains more than 90% of enzymatic activity between pH 4.5–6.5 after treatment for 1 hour in 0.1M citric acid/trisodium phosphate buffer.

14. The DNA sequence according to claim 13, in which said DNA sequence is isolated from a DNA library of Aspergillus.

15. The DNA sequence according to claim 13, in which said DNA sequence is isolated from a DNA library of *Aspergillus aculeatus*.

16. The DNA sequence according to claim 13, in which said DNA sequence is isolated from a DNA library of *Aspergillus aculeatus*, CBS 101.43.

17. A recombinant expression vector comprising the DNA sequence according to claim 13.

18. A cell comprising the recombinant expression vector according to claim 17.

19. The cell according to claim 18 in which said cell is a eucaryotic cell.

20. The cell according to claim 18, in which said cell is a fungal cell.

21. The cell according to claim 18, in which said cell is a yeast cell or filamentous fungal cell.

22. The cell according to claim 18, in which said cell belongs to a strain of Aspergillus.

23. The cell according to claim 18, in which said cell belongs to a strain of *Aspergillus niger* or *Aspergillus oryzae*.

24. A method of producing an enzyme exhibiting polygalacturonase activity comprising culturing the cell of claim 18 under conditions permitting the production of the enzyme and recovering the enzyme from the culture.

* * * * *